United States Patent
Nitta

(10) Patent No.: US 11,305,089 B2
(45) Date of Patent: Apr. 19, 2022

(54) HUMIDIFIER AND RESPIRATORY ASSISTANCE DEVICE

(71) Applicant: Metran Co., Ltd., Kawaguchi (JP)

(72) Inventor: Kazufuku Nitta, Saitama (JP)

(73) Assignee: Metran Co., Ltd., Kawaguchi (JP)

(*) Notice: Subject to any disclaimer, the term of this patent is extended or adjusted under 35 U.S.C. 154(b) by 833 days.

(21) Appl. No.: 16/092,891

(22) PCT Filed: Apr. 11, 2017

(86) PCT No.: PCT/JP2017/014810
§ 371 (c)(1),
(2) Date: Oct. 11, 2018

(87) PCT Pub. No.: WO2017/179569
PCT Pub. Date: Oct. 19, 2017

(65) Prior Publication Data
US 2019/0134342 A1    May 9, 2019

(30) Foreign Application Priority Data

Apr. 13, 2016  (JP) .............................. JP2016-080251
Jun. 23, 2016  (JP) .............................. JP2016-124251

(51) Int. Cl.
*A61M 16/10* (2006.01)
*A61M 16/16* (2006.01)
(Continued)

(52) U.S. Cl.
CPC ........ *A61M 16/109* (2014.02); *A61M 11/002* (2014.02); *A61M 11/003* (2014.02);
(Continued)

(58) Field of Classification Search
CPC ............ A61M 16/0808; A61M 16/107; A61M 16/1095; A61M 16/08; A61M 16/105; A61M 16/106
See application file for complete search history.

(56) References Cited

U.S. PATENT DOCUMENTS

| 4,921,642 A | 5/1990 | LaTorraca |
| 8,939,152 B2 | 1/2015 | Wondka et al. |

(Continued)

FOREIGN PATENT DOCUMENTS

| CN | 103124575 A | 5/2013 |
| CN | 204379943 U | 6/2015 |

(Continued)

OTHER PUBLICATIONS

Search Report of the European Patent Office issued in European Application No. 17 78 2382 in the English language, dated Mar. 26, 2019 (4 pages).

(Continued)

*Primary Examiner* — Margaret M Luarca
*Assistant Examiner* — Cana A Gallegos
(74) *Attorney, Agent, or Firm* — Flynn Thiel, P.C.

(57) ABSTRACT

A humidifier that can easily control temperature and humidity in an independent manner, irrespective of a flow rate of medical gas to be supplied, is provided. The humidifier is connected to a respiratory assistance device configured to regulate or assist ventilation of a user. The humidifier is configured to add moisture to gas fed from a gas source in the form of fine particles or water vapor. The humidifier includes a liquid container configured to contain liquid containing at least water, a mist-droplet generation unit configured to generate mist droplets being fine particles of the liquid, and a water retaining member configured to hold at least a part of the mist droplets.

3 Claims, 11 Drawing Sheets

(51) Int. Cl.
  *A61M 11/06* (2006.01)
  *A61M 16/06* (2006.01)
  *A61M 11/00* (2006.01)
  *A61M 16/08* (2006.01)
  *A61M 16/00* (2006.01)

(52) U.S. Cl.
  CPC ........... *A61M 11/005* (2013.01); *A61M 11/06* (2013.01); *A61M 16/0003* (2014.02); *A61M 16/0666* (2013.01); *A61M 16/0672* (2014.02); *A61M 16/0808* (2013.01); *A61M 16/0816* (2013.01); *A61M 16/107* (2014.02); *A61M 16/1055* (2013.01); *A61M 16/1095* (2014.02); *A61M 16/16* (2013.01); *A61M 16/162* (2013.01); *A61M 16/0875* (2013.01); *A61M 2016/0039* (2013.01); *A61M 2205/3368* (2013.01); *A61M 2205/3653* (2013.01); *A61M 2205/7536* (2013.01)

(56) References Cited

U.S. PATENT DOCUMENTS

| | | | |
|---|---|---|---|
| 2001/0050080 A1 | 12/2001 | Seakins et al. | |
| 2009/0025724 A1* | 1/2009 | Herron, Jr. | A61M 16/0875 128/204.18 |
| 2010/0083965 A1* | 4/2010 | Virr | A61M 16/109 128/203.26 |
| 2010/0206308 A1* | 8/2010 | Klasek | A61M 16/1085 128/203.27 |
| 2012/0012108 A1* | 1/2012 | Sata | A61M 16/1075 128/203.14 |
| 2012/0125334 A1* | 5/2012 | Korneff | A61M 16/109 128/203.26 |
| 2012/0138050 A1* | 6/2012 | Wondka | A61M 11/042 128/200.16 |
| 2013/0263845 A1* | 10/2013 | Arcilla | A61M 11/006 128/200.14 |
| 2014/0158127 A1* | 6/2014 | Boucher | A61M 16/14 128/203.22 |
| 2018/0078728 A1* | 3/2018 | Holyoake | A61M 16/0497 |

FOREIGN PATENT DOCUMENTS

| | | |
|---|---|---|
| JP | 55157634 U | 4/1979 |
| JP | 5575143 A | 6/1980 |
| JP | 62-99252 U | 6/1987 |
| JP | 2-224765 A | 9/1990 |
| JP | 2001241709 A | 9/2001 |
| JP | 2005-177521 A | 7/2005 |
| JP | 2009127944 A | 6/2009 |
| JP | 2012122671 A | 6/2012 |
| JP | 2014-501131 A | 1/2014 |
| WO | WO 03/061746 A1 | 7/2003 |
| WO | WO 2010/116846 A1 | 10/2010 |
| WO | 2012045051 A1 | 4/2012 |
| WO | WO 2016/036260 A1 | 3/2016 |

OTHER PUBLICATIONS

Japanese Office Action issued in corresponding Japanese Application No. 2018-512019 dated Nov. 10, 2020 (10 pages).
International Search Report issued in Application No. PCT/JP2017/014810 dated Jul. 18, 2017 and English translation (5 pages).
Written Opinion issued in Application No. PCT/JP2017/014810 dated Jul. 18, 2017 (5 pages).
Chinese Office Action issued in corresponding China Patent Application No. 201780023531.4 dated Jun. 12, 2020 (11 pages).

* cited by examiner

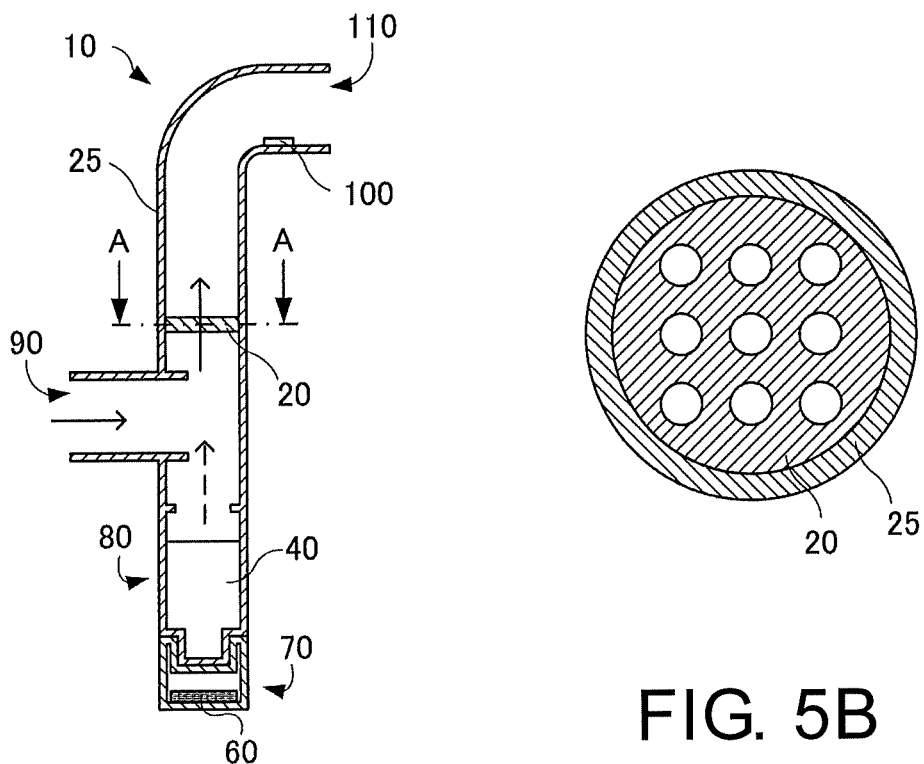
FIG. 5A
FIG. 5B
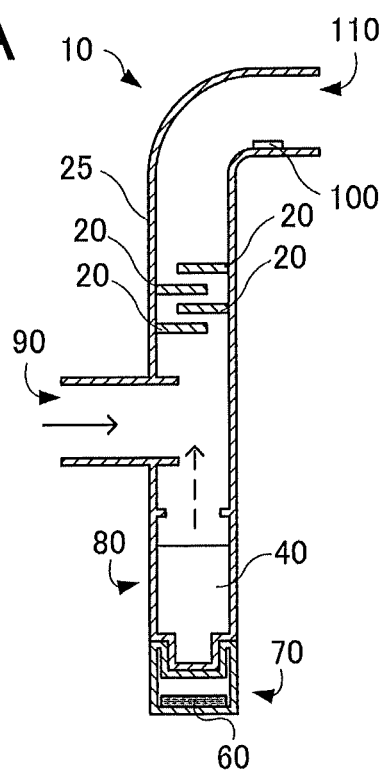
FIG. 5C

HUMIDIFIER AND RESPIRATORY ASSISTANCE DEVICE

TECHNICAL FIELD

The present invention relates to a humidifier that humidifies a gas fed from a respiratory assistance device such as an artificial respirator, a CPAP (continuous positive airway pressure) device, or an oxygen breathing apparatus.

BACKGROUND ART

Breathing for inspiring oxygen and expiring carbon dioxide is vital to life maintenance of human beings. In the case of a breathing disorder owing to paralysis of a breathing muscle, collapse of alveoli, or the like, a so-called artificial respirator is used for supporting spontaneous breathing. In the artificial respirator, a gas (medical gas) fed to a user is composed of compressed air or oxygen gas. Since the gas is supplied from a gas cylinder or medical gas piping equipment, the gas has a lower temperature than a body temperature and is very dry. If the medical gas having the uncontrolled temperature and humidity is supplied to the user's respiratory system, the gas may cause dryness and damage in respiratory mucosa, fixation of sputum, and the like, as well as causing discomfort, and hence may cause pneumonia in some instances. To prevent such a disorder, it is necessary for the artificial respirator to heat and humidify inspiratory air. There are no common standards for the temperature and humidity of the inspiratory air of the artificial respirator. However, it is said that, as to the inspiratory air, a temperature of 32 or more degrees centigrade and a relative humidity of the order of 75% to 100% are appropriate. In tracheal intubation, in particular, it is said that a temperature of 37 degrees centigrade and a relative humidity of 100% are preferable.

Accordingly, conventional respiratory assistance devices, such as artificial respirators, CPAP (continuous positive airway pressure) devices, and oxygen breathing apparatuses are provided with humidifiers (see FIG. 10A). A respiratory assistance device 1 is composed mainly of a gas source (ventilator) 280, a humidifier 10, a breathing circuit 105, and a mask 260. A medical gas supplied from the gas source (ventilator) 280 absorbs moisture in the humidifier 10, and is supplied to a user P through the breathing circuit 105.

Most of the currently used humidifiers adopt a method in which water vapor that is produced by heat vaporization of liquid water is introduced into a medical gas and supplied to a user (see, for example, Japanese Patent Application Laid-Open No. 2005-177521). FIG. 10B shows an example of a configuration of a conventional humidifier. The humidifier 10 is composed mainly of a humidification chamber 220, a heater 290, and a controller 130. The controller 130 feedback-controls the heater 290 and the like, while monitoring a thermometer 100 and a thermometer 240 near a user (see FIG. 10A). Water 40 stored in the humidifier 10 is heated by the heater 290, whereby water vapor is generated. A dry medical gas fed from a ventilator-side pipe 90 is humidified and has an increased vapor pressure during the passage of the gas through the humidification chamber 220 filled with the water vapor, and is then fed to the breathing circuit 105 through a breathing circuit-side pipe 110 (see FIG. 10A). The breathing circuit 105 is often provided with an anti-condensation heating unit 270 configured to prevent condensation in the circuit.

Even in the CPAP (continuous positive airway pressure) devices and the like, humidification is required, when outside air introduced is dry.

SUMMARY OF INVENTION

Technical Problem

In the so-called steam humidifier, as described above, it is difficult to control temperature and humidity in an independent manner. FIG. 11 shows a saturated vapor pressure curve at 1 atmospheric pressure. A vertical axis represents saturated vapor pressure, and a horizontal axis represents temperature. For example, in a case where the medical gas is supplied at a high flow rate, a large amount of water vapor is required to be produced. However, as shown in FIG. 11, the upper limit of the amount of water vapor that air can contain, in other words, the upper limit of the partial pressure of water vapor (vapor pressure) in air depends on temperature. Therefore, for example, in a state of B at 40 degrees centigrade, the vapor pressure cannot be physically changed to a value as high as that at a point D at 100 degrees centigrade. Accordingly, it is required to prepare the large-volume humidification chamber 220 (see FIG. 10B) and vaporize a large amount of water by boiling. In this case, however, there is concern that the temperature of the fed gas rises too high. On the contrary, in a case where the medical gas is supplied at a low flow rate, the water vapor itself used for humidification can be easily produced, even if the temperature inside the humidification chamber 220 is lower than the boiling point of water, i.e. 100 degrees centigrade, for example, at a point C of FIG. 11. However, even when the temperature is 80 degrees centigrade corresponding to a point C of FIG. 11 and the relative humidity is 100% in the breathing circuit immediately near the humidification chamber 220, if the temperature drops on its way to the breathing circuit 105 to a point A (20 degrees centigrade) of FIG. 11, water vapor is liquified by an amount of H due to condensation, and the water vapor is thereby lost from the fed gas. As a result, when the fed gas is supplied to the user P, if the temperature is raised to the point B (40 degrees centigrade) of FIG. 11, the water vapor contained in the gas has been reduced due to the condensation, because the vapor pressure at the point A (20 degrees centigrade) is low. This results in an abrupt reduction in the relative humidity. The condensation in the breathing circuit may cause growth of bacteria, and is not preferable.

Considering the circumstances described above, the present invention aims at providing a humidifier that can easily control temperature and humidity in an independent manner irrespective of a flow rate of medical gas to be supplied.

Solution to Problem (1) The present invention provides a humidifier that is to be connected to a respiratory assistance device configured to regulate or assist ventilation of a user. The humidifier is configured to add moisture to a gas fed from a gas source in the form of fine particles or water vapor. The humidifier includes a liquid container configured to contain a liquid containing at least water, a mist-droplet generation unit configured to generate mist droplets being fine particles of the liquid, and a water retaining member configured to hold at least a part of the mist droplets.

The mist droplets, i.e. the fine particles of the liquid having diameters of several micrometers to several tens of micrometers, have larger surface areas per unit volume, and therefore are easily vaporized. According to the invention described in (1) above, the generation of the mist droplets, i.e. the fine particles (minute droplets) of the water contained in the liquid, promotes the vaporization into the water vapor, and at the same time, the water held by the water retaining member evaporates. Therefore, it is possible to realize the humidifier that humidifies the gas fed from the gas source with high efficiency.

(2) The present invention provides the humidifier described in (1) above, in which the water retaining member is provided inside an inspiratory pipe of a breathing circuit provided in the respiratory assistance device along a longitudinal direction of the inspiratory pipe, and the water retaining member has a length of 50 cm or more.

The invention described in (2) above has extremely significant effects that, since the water retaining member has an extremely large surface area, the moisture held by the water retaining member is easily vaporized. When the water retaining member containing the moisture is present along an interior wall of the inspiratory pipe, if the inspiratory pipe of the breathing circuit is heated with an anti-condensation heater attached thereto, the majority of the heat is used for the evaporation of the moisture from the water retaining member. Therefore, the invention described in (2) above has the beneficial effect of preventing an increase in temperature of the inspiratory pipe.

(3) The present invention provides the humidifier described in (1) or (2) above, in which the water retaining member has gas permeability, and has a tubular structure that is closed at one end on a side of the user and has an opening at the other end on a side of the gas source, and the gas penetrates the inside of the water retaining member through the opening, passes through the water retaining member, and is released to the outside thereof.

According to the invention described in (3) above, the water retaining member has a structure of which one end on the side of the user is closed. The water retaining member thus allows the medical gas containing the water vapor to pass therethrough, while blocking liquid water. Therefore, the water retaining member itself, which performs humidification, can filter the gas. In other words, the water retaining member has the beneficial effect of functioning as a so-called bacteria filter.

(4) The present invention provides the humidifier described in any one of the above (1) to (3), including a droplet heating unit configured to heat at least one of the mist droplets and the moisture held by the water retaining member to vaporize the mist droplets or the moisture into the water vapor.

According to the invention described in (4) above, it is possible to generate the water vapor with a lower energy than general vaporization by boiling, to humidify the fed gas. Since a large amount of water vapor can be generated without boiling the whole stored water, the invention described in (4) above has the beneficial effect that the heated humidity can be controlled without excessively increasing the temperature of the gas.

(5) The present invention provides the humidifier described in any one of (1) to (4) above, in which the droplet heating unit is provided in an inscribed or circumscribed manner in or on an inspiratory pipe of a breathing circuit provided in the respiratory assistance device.

The invention described in (5) above has the beneficial effect that, since the droplet heating unit, such as a heater, configured to heat the mist droplets to make them into the water vapor is provided in the inspiratory pipe of the breathing circuit, humidification can be performed using evaporation of the mist droplets while condensation that easily occurs in the inspiratory pipe can be prevented.

(6) The present invention provides the humidifier described in any one of (1) to (5) above, in which the droplet heating unit is provided in an inscribed or circumscribed manner in or on the water retaining member.

The invention described in (6) above has the beneficial effect that, since the droplet heating unit, such as a heater, configured to heat the mist droplets to make them into the water vapor is provided in an inscribed or circumscribed manner in or on the water retaining member disposed in the inspiratory pipe of the breathing circuit, humidification can be performed using evaporation of the moisture held by the water retaining member. When the droplet heating unit is provided inside the water retaining member, the provision of the droplet heating unit facilitates keeping the shape of the soft water retaining member 20, thus having the effect of securing a surface area for evaporation.

(7) The present invention provides the humidifier described in any one of (1) to (6) above, in which the vapor pressure of the gas is increased by moisture held by the water retaining member.

The invention described in (7) above has the beneficial effect that, in addition to the water vapor obtained by vaporization of the mist droplets, i.e. the minute droplets of water, the moisture adhering to the water retaining member evaporates into water vapor in the gas, thus allowing further humidification.

(8) The present invention provides the humidifier described in any one of (1) to (7) above, in which the water retaining member is an exchangeable member.

Bacteria easily grow in a place where moisture is present. The invention described in (8) above has the beneficial effect that, since the water retaining member is an exchangeable member, it is possible to easily solve the problem of how to keep the respiratory assistance device in a good hygiene state, which is an extremely important problem for the respiratory assistance device.

(9) The present invention provides the humidifier described in any one of (1) to (8) above, in which the water retaining member has a water absorbing property.

If the water retaining member has no water absorbing property, when condensed water covers the surface of the water retaining member, the water vapor permeability of the water retaining member extremely drops. The invention described in (9) above has the beneficial effect that, since the water retaining member has the water absorbing property, the condensed water is absorbed by the water retaining member, and the minute pores through which the water vapor passes are kept open, and therefore the permeability of the water vapor hardly decreases.

(10) The present invention provides the humidifier described in any one of (1) to (9) above, in which the water retaining member is made of a nonwoven fabric.

According to the invention described in (10) above, since the nonwoven fabric has no directional property in its strength and extensibility, inexpensiveness, and ease of regulation of the size of thickness and a gap, it is possible to provide the water absorptive retaining member that does not allow the mist droplets to pass therethrough, while allowing the water vapor to pass therethrough.

(11) The present invention provides the humidifier described in any one of (1) to (10) above, in which a part of the gas passes through the inside of the water retaining member, while a remaining part of the gas does not pass through the inside of the water retaining member.

The invention described in (11) above has the beneficial effect that, since, when a part of dry gas passes through a space (a space on the side of the humidifier in the water retaining member), the vapor pressure tends to increase, and humidification is thus easily performed. A part of the fed gas does not pass through the inside of the water retaining member, thus having the effect of reducing a resistance in breathing.

(12) The present invention provides the humidifier described in (11) above, in which one end of the water retaining member that is open on the side of the gas source is joined to an inner peripheral surface of the humidifier, and the water retaining member closes a passage through which the gas flows.

According to the invention described in (12) above, since both ends of the water retaining member are closed with respect to the inspiratory pipe, the inside of the humidifier is separated from the breathing circuit. Therefore, the water retaining member allows the medical gas containing the water vapor to pass therethrough, and does not allow the liquid water to pass therethrough. In other words, the water retaining member itself, which performs humidification, can filter the gas. Therefore, the water retaining member offers a beneficial effect as a bacteria filter.

(13) The present invention provides the humidifier described in any one of (1) to (12) above, in which the humidifier has a passage through which the gas flows, the passage is closed by the water retaining member, and the water retaining member partitions the passage into an upstream side that is on a side of the gas source and has the liquid container and the mist-droplet generation unit, and a downstream side that is on a side of the user.

Since the mist droplets, being the liquid fine particles, have diameters of several micrometers to several tens of micrometers and are much larger in size than the water vapor (molecules of water) in units of angstrom, the mist droplets tend to contain bacteria and viruses. According to the invention described in (13) above, the water retaining member, which does not allow the mist droplets to pass therethrough, partitions a part in which the mist droplets are generated, and therefore the bacteria, the viruses, and the like contained in the mist droplets are prevented from being conveyed from the liquid container or the mist-droplet generation unit to the user. In other words, since the water retaining member itself filters the gas, the water retaining member offers a beneficial effect as a bacteria filter.

(14) The present invention provides the humidifier described in any one of (1) to (3) above, in which the mist-droplet generation unit has a liquid heating unit configured to heat the liquid to evaporate the water contained in the liquid.

The invention described in (14) above has the beneficial effect that, since the water stored in the liquid container can be used for humidification, while being sterilized by heating, the humidifier is easily kept in a good hygiene state.

(15) The present invention provides the humidifier described in any one of (4) to (13) above, in which the mist-droplet generation unit has a liquid heating unit configured to heat the liquid to evaporate the water contained in the liquid, and the liquid heating unit is integrated with the droplet heating unit.

The invention described in (15) above has the beneficial effect that, since the liquid heating unit configured to heat the liquid is integrated with the droplet heating unit configured to heat the mist droplets, temperature control is easily performed.

(16) The present invention provides the humidifier described in any one of (1) to (15) above, in which the mist-droplet generation unit has an ultrasonic generation unit configured to vibrate the liquid to generate the mist droplets.

The invention described in (16) above has the effect that, since the mist droplets, being the minute water droplets, can be easily generated in a surface of the liquid stored in the liquid container, humidification can be performed with a low energy. The invention described in (16) above has the beneficial effect of easily varying a mist droplet generation amount by varying the amplitude of vibration of the ultrasonic oscillator, and therefore easily controlling the humidity.

(17) The present invention provides the humidifier described in any one of (1) to (16) above, in which the mist-droplet generation unit includes a vibration generation device and a mesh having many minute pores.

The invention described in (17) above has the beneficial effect that, since the mist-droplet generation unit can be easily miniaturized, the humidifier having good transportability can be provided.

(18) The present invention provides the humidifier described in any one of (1) to (17) above, in which the mist-droplet generation unit has a jet-type mist-droplet generation unit configured to use compressed air.

The invention described in (18) above has the beneficial effects of having simple structure and ease of maintenance, thus being easily kept in a good hygiene state.

(19) The present invention provides the humidifier described in any one of (1) to (18) above, in which the water retaining member is further disposed in the vicinity of a nasal prong configured to feed the gas to nasal cavities of the user.

When condensation occurs in the vicinity of the nasal prong, droplets may enter the respiratory tract with the medical gas. Since bacteria easily breed in liquid water, the entry of the droplets into the respiratory tract may cause pneumonia. Disposing the water retaining member in the vicinity of the nasal prong has the significant effect of preventing the droplets from entering the respiratory tract, by absorbing the condensed droplets.

(20) The present invention provides the humidifier described in (19) above, in which a housing configured to support the nasal prong has at least one drain hole configured to drain condensation.

Since the housing configured to support the nasal prong is disposed in the vicinity of the nasal cavities and generally has a lower temperature than a body temperature, water vapor in breath tends to condense to droplets and accumulate. If the droplets are left as is, bacteria easily breed there. The invention described in (20) above has the beneficial effect that, since the housing configured to support the nasal prong includes the drain hole to drain condensation, the droplets can drain from the drain hole in an appropriate manner, whereby the housing can be kept in a good hygiene state.

(21) The present invention provides the humidifier described in any one of (1) to (20) above, in which the water retaining member is divided into at least two members which are disposed separately.

The water retaining member on the side of the humidifier is always supplied with mist droplets, and is in a wet state, in principle. On the contrary, the water retaining member disposed in the vicinity of the nasal prong aims at absorbing water, and is preferably dry. Therefore, as described in the invention of (21) above, by dividing the water retaining member into at least two members, the resulting water retaining members can have different roles, such that one is for humidification and the other is for absorption of water.

(22) The present invention provides a humidifier connected to a respiratory assistance device configured to regulate or assist ventilation of a user. The humidifier is configured to make liquid containing at least water into mist droplets, make a water retaining member temporarily hold the mist droplets, make fed gas be brought into contact with the water retaining member to humidify the gas, and supply a user with the humidified gas.

According to the invention described in (22) above, the water stored in the liquid container is made into the mist droplets, i.e. minute droplets, that are easily vaporized, and thereafter is heated to be made into water vapor, thus allowing easy humidification. Since a large amount of water vapor can be generated without heating the whole stored water, temperature and humidity are independently controlled with ease. Since the humidified gas is filtered with the nonwoven fabric, the invention described in (22) above has the beneficial effects that the nonwoven fabric can also function as a bacteria filter.

(23) The present invention provides a respiratory assistance device configured to regulate or assist ventilation of a user, and the respiratory assistance device has the humidifier provided with the features described in (1) to (22) above.

The invention described in (23) above has the beneficial effect that it is possible to provide the respiratory assistance device including the humidifier that can independently regulate the temperature and humidity, even with a high flow rate or a low flow rate.

Advantageous Effects of Invention

The present invention provides a humidifier that is connected to a respiratory assistance device configured to regulate or assist ventilation of the user. The humidifier is configured to make the liquid containing at least the water into mist droplets, make the water retaining member temporarily hold the mist droplets, make the fed gas be brought into contact the water retaining member to humidify the gas, and supply the user with the humidified gas. The present invention also provides a respiratory assistance device including the humidifier.

According to the present invention, since the generation of the mist droplets, i.e. the minute water particles contained in the liquid, promotes the vaporization to the water vapor, the humidifier that humidifies the gas fed to the user can be realized. The present invention has the beneficial effect that, since the humidifier has the water retaining member configured to hold at least a part of the mist droplets in a liquid form, the moisture adhering to the water retaining member can further humidify the gas.

BRIEF DESCRIPTION OF DRAWINGS

FIG. 5A is a cross-sectional view of a humidifier according to a fifth embodiment of the present invention.
FIG. 5B is a cross cross-sectional view taken along line A-A of FIG. 5A.
FIG. 5C is a cross-sectional view of a humidifier according to a sixth embodiment of the present invention.

DESCRIPTION OF EMBODIMENTS

Figure 1:
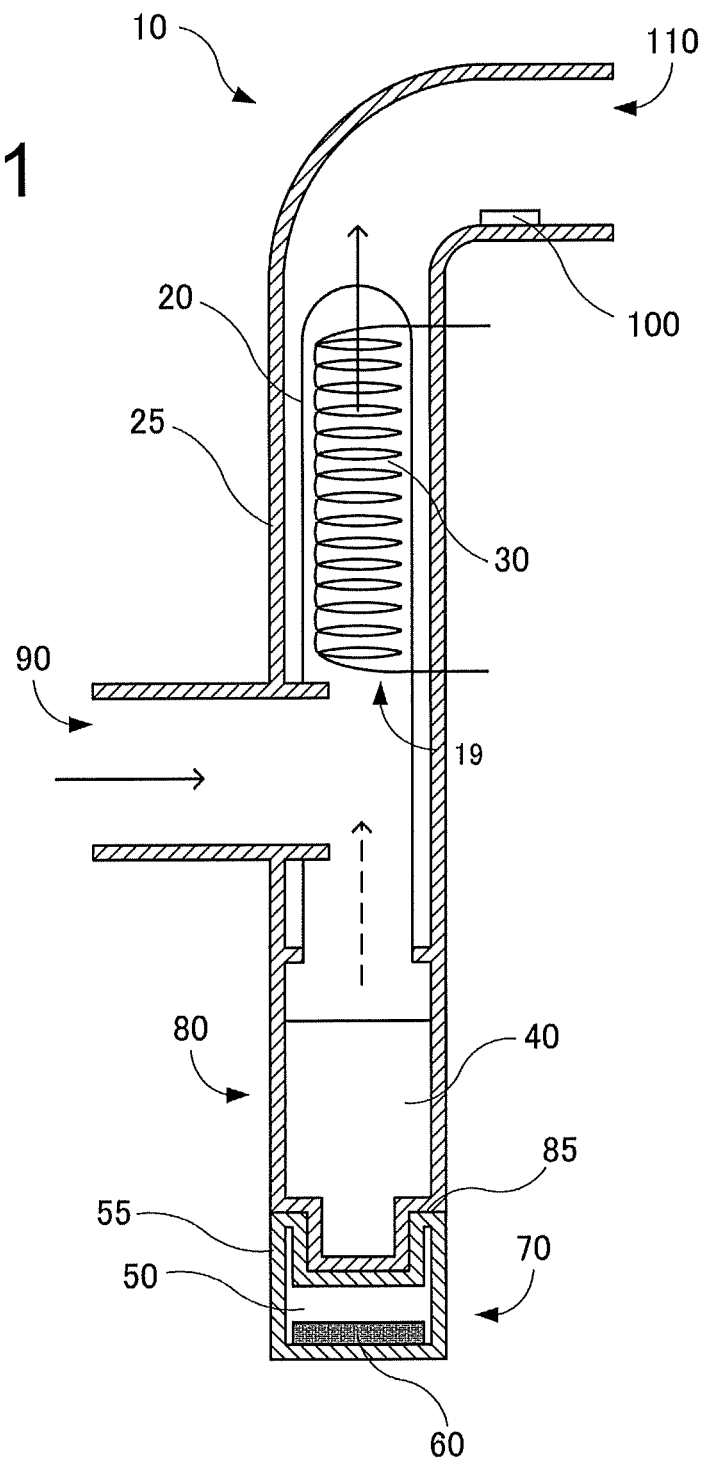
FIG. 1 is a cross-sectional view of a humidifier according to a first embodiment of the present invention.

Embodiments of the present invention will be described below with reference to the attached drawings.

FIGS. 1 to 9 show an example of the embodiments of the present invention. In the drawings, components indicated with the same reference numerals are identical components, and the fundamental configuration thereof is the same as conventional one shown in the drawings. In each of the drawings, the configuration is partly omitted for the sake of simplicity of the drawings. The size, shape, thickness, and the like of components are emphasized in an appropriate manner.

Figure 10A:
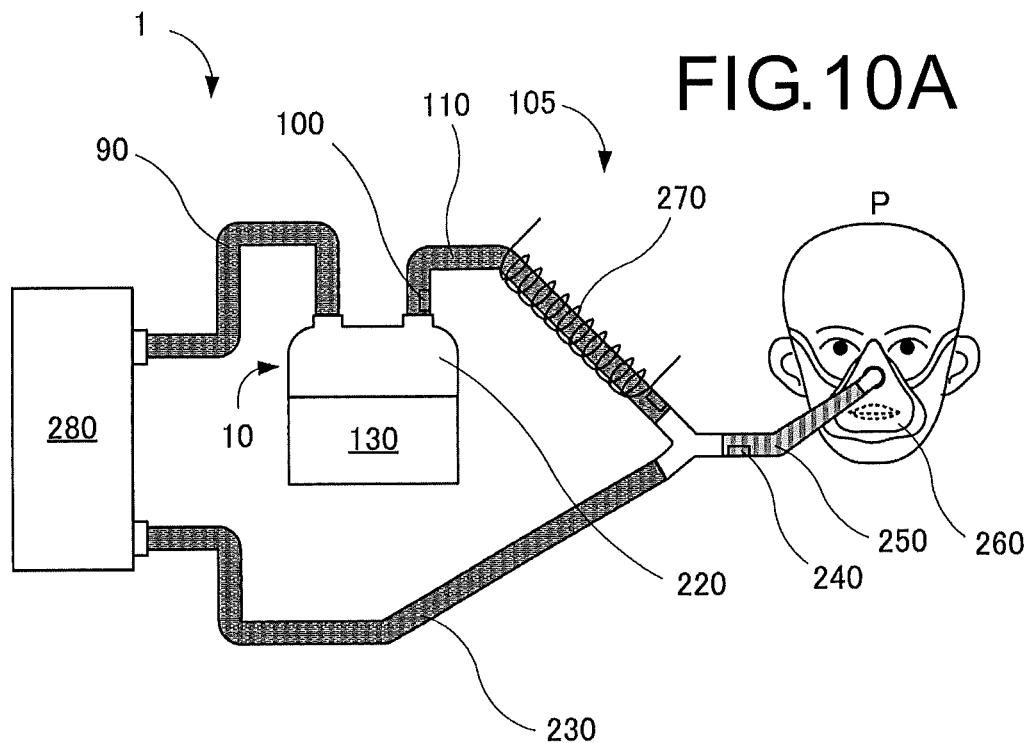
FIG. 10A is an explanatory view showing a configuration of a conventional respiratory assistance device.
Figure 10B:
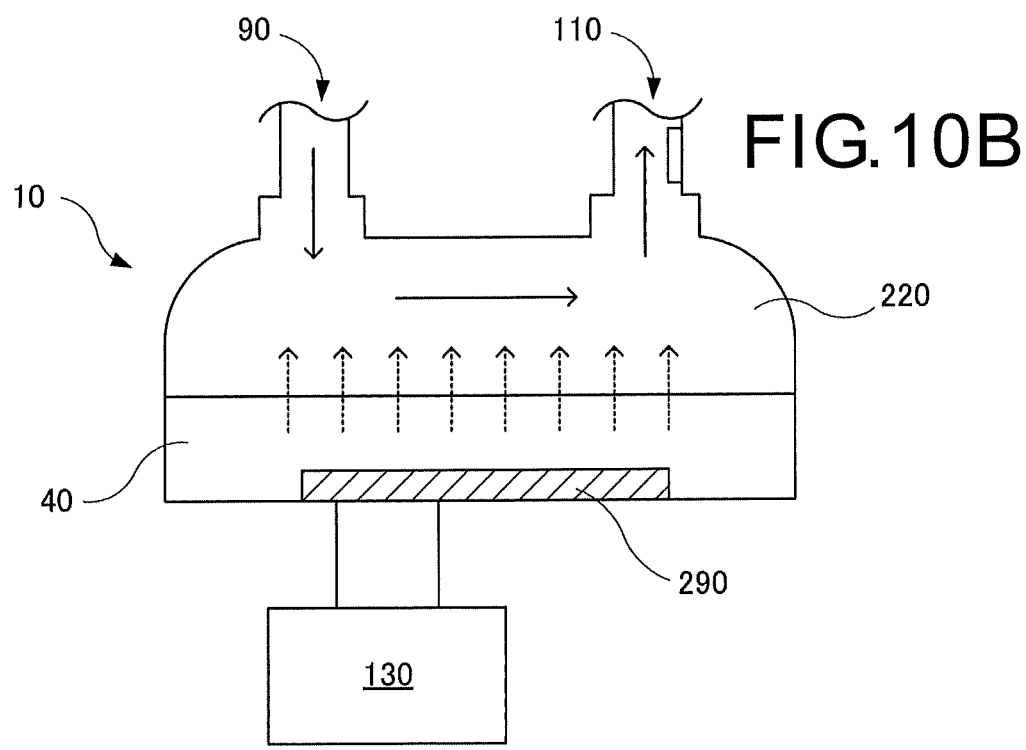
FIG. 10B is an explanatory view showing a configuration of a conventional steam humidifier.
Figure 11:
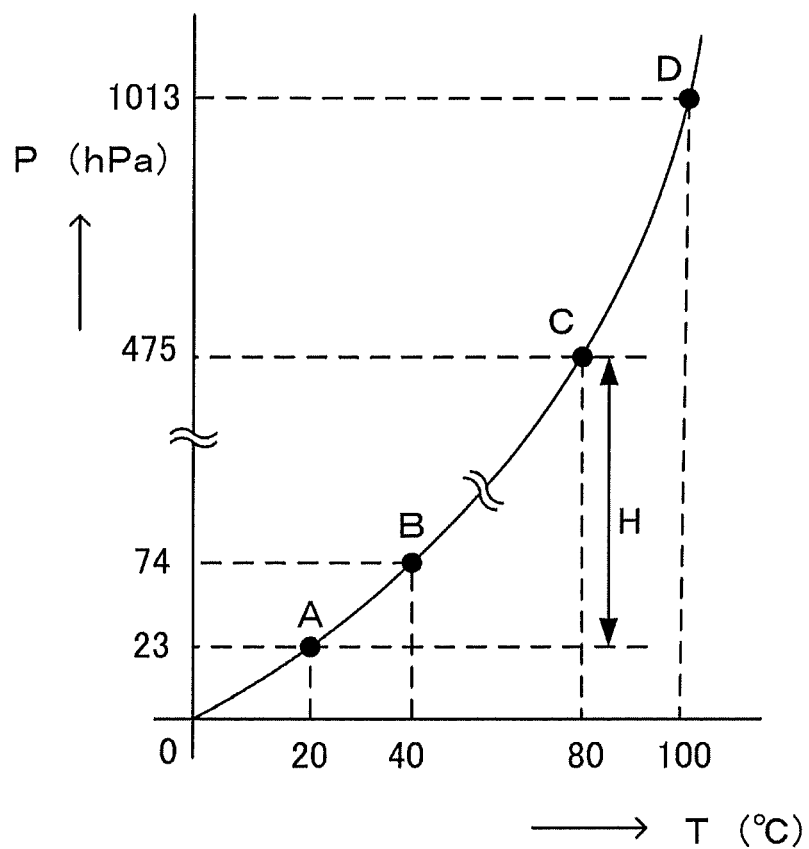
FIG. 11 is a saturated vapor pressure curve of water at 1 atmospheric pressure.

FIG. 1 is a cross-sectional view of a humidifier 10 according to a first embodiment of the present invention. The humidifier 10, just as with the conventional humidifier 10 provided in the conventional respiratory assistance device (see FIG. 10A), is connected to a respiratory assistance device configured to regulate or assist ventilation in a respirator of a user, to add moisture in the form of fine particles or water vapor to a gas fed from a gas source. To be more specific, the humidifier is connected between a gas source (ventilator) 280 of a medical gas and a mask 260 (see FIG. 10 A) configured to supply the user with the medical gas. The humidifier 10 is disposed between a ventilator-side pipe 90 and a breathing circuit-side pipe 110. The humidifier 10 includes a liquid container 80 configured to contain liquid including at least water, a mist-droplet generation unit 70 configured to generate mist droplets, i.e. minute droplets of the liquid, and a water retaining member 20 configured to hold at least a part of the mist droplets. In the present embodiment, the mist-droplet generation unit 70 is caused to generate the mist droplets by ultrasonic vibration, as described later.

The mist-droplet generation unit 70 has an ultrasonic generation unit configured to generate the mist droplets by adding vibration to the liquid. In other words, in the humidifier according to the first embodiment, the mist-droplet generation unit 70 is an ultrasonic mist-droplet generation unit configured to use so-called cavitation effect that generates air bubbles on a liquid surface by a vibration energy from an ultrasonic oscillator. The mist-droplet generation unit 70 includes a case 55, an ultrasonic oscillator 60, and an ultrasonic transfer material 50. The ultrasonic transfer material 50 is, for example, water. The water that is the ultrasonic transfer material 50 held in the case 55, as well as water 40 that is brought into contact with the case 55 through a case 25, has a high specific heat, and hence has high resistant to increase in temperature. Therefore, the water is suitable for long time use on the whole of the humidifier 10. The mist-droplet generation unit 70 and the liquid container 80 are tightly attached to each other through an ultrasonic transferable material, such as a nonvolatile oil, at a boundary 85 therebetween.

The ultrasonic oscillator 60 is controlled by a controller 130 (not illustrated). The controller 130 includes a CPU, a RAM, a ROM, and the like to perform entire control of the humidifier 10. The CPU is a so-called central processing unit that performs various functions by execution of various types of programs. The RAM is used as an operation area and a memory area of the CPU. The ROM stores an operating system and the programs executed by the CPU. The controller 130 preferably has the functions of monitoring a thermometer 100, a thermometer (not illustrated) in the vicinity of the mask 260 (see FIG. 10A) that the user wears, a flowmeter (not illustrated) for the fed gas, and the like, and performing feedback control (PID control) of a heater and the like of a droplet heating unit 30, to perform adjustment at a predetermined temperature and humidity. When the amount of the water 40 contained in the liquid container 80 becomes a predetermined level or less, a warning is preferably issued.

A mist-droplet generation amount by the mist-droplet generation unit 70 is controlled by the controller 130. For example, when an alternating current voltage to be applied to the ultrasonic oscillator 60 has an increased amplitude, the vibration of the ultrasonic oscillator 60 has an increased amplitude, and therefore the mist-droplet generation amount is increased. The liquid container 80 may be preferably taken out of the case 25. The mist-droplet generation unit 70 may also be preferably taken out of the liquid container 80.

The humidifier 10 has a passage configured to allow the fed gas to pass therethrough. The passage is closed by the water retaining member 20. The water retaining member 20 partitions the passage into an upstream side that is on the side of the gas source (ventilator) 280 and has the liquid container 80 and the mist-droplet generation unit 70, and a downstream side that is on the side of the user.

To be more specific, the water retaining member 20 has gas permeability, and has a tubular structure that is closed at one end on the side of the user, and is open at the other end on the side of the gas source (ventilator) 280. The gas penetrates the inside of the water retaining member 20 through an opening 19, passes through the water retaining member 20, and is released into the breathing circuit-side pipe 110. The opening 19 of the tube of the water retaining member 20 is joined to an inner peripheral surface of the case 25 at its end part, so as to close the passage.

To reduce the resistance of the gas passing through the water retaining member 20, a gas flow area is preferably increased. Therefore, a spacer is preferably provided between the tubular water retaining member 20 and the inner peripheral surface of the case 25, to secure a gap therebetween. Instead of providing the spacer, the diameter of the tube of the water retaining member 20 may be made sufficiently smaller than the internal diameter of the case 25, to secure a gap therebetween. The water retaining member 20 is preferably made of a water absorptive nonwoven fabric, and is preferably an exchangeable member. The material of the nonwoven fabric of the water retaining member 20 is, for example, polypropylene to which a surface-active agent treatment, a fluoride gas treatment, a sulfonation treatment, an acrylic acid graft treatment, a plasma discharge treatment, or the like is preferably applied to impart hydrophilicity thereto.

The water retaining member 20 is disposed in the case 25. The droplet heating unit 30, which heats at least one of droplets, i.e., the mist droplets and moisture held in the water retaining member and vaporizes the mist droplets or the moisture into water vapor, is disposed inside the water retaining member 20 on the side of the liquid container 80. The droplet heating unit 30 is a resistance heater made of, for example, a nichrome wire or the like, and is connected to a power supply (not illustrated). The controller 130 controls electric power on the basis of the temperature detected by the thermometer 100 and the like, to control temperature and humidity. The water retaining member 20 blocks the mist droplets, while allowing gas containing the water vapor to pass therethrough.

Next, the operation of the above-described embodiment will be described with reference to FIG. 1.

A dry medical gas is supplied from the ventilator-side pipe 90 to the humidifier 10. The role of the humidifier 10 is to add moisture to the medical gas, and humidification is performed by the following two methods.

(1) The droplet heating unit 30 vaporizes mist droplets being generated in a surface of the liquid container 80 into water vapor. An ultrasonic vibration energy generated by the ultrasonic oscillator 60 is transmitted to a water surface of the liquid container 80. By weakening surface tension at a part of the water surface, the minute mist droplets are generated. Since the mist droplets are minute droplets having a large surface area relative to its volume, the mist droplets are easily vaporized. When the mist droplets reach the vicinity of the droplet heating unit 30 where the temperature is high and the saturated vapor pressure is large, the mist droplets are more easily vaporized. As a result, the water vapor generated by the vaporization humidifies the dry medical gas.

(2) Mist droplets being generated in the surface of the liquid container 80 reach the water retaining member 20, and adhere to the water retaining member 20. Since the water retaining member 20 has a water absorbing property, moisture adhering to the water retaining member is held as water in a liquid form. When the gas fed from the ventilator-side pipe 90 passes in the vicinity of the water retaining member 20, the vapor pressure of the gas is further increased by the moisture held by the water retaining member 20, and therefore the gas is humidified.

As described above, in the humidifier 10 according to the first embodiment, the water vapor for humidification is generated with a lower energy than general vaporization by boiling. Since a large amount of water vapor can be generated without boiling the stored water 40, the humidifier 10 has the beneficial effect of controlling the humidity independently of the temperature, without excessively increasing the temperature of the medical gas. Since the water retaining member 20 filters the fed gas, the water retaining member 20 has the effect of playing a role as a bacteria filter, as well as a humidifier.

Figure 2A:
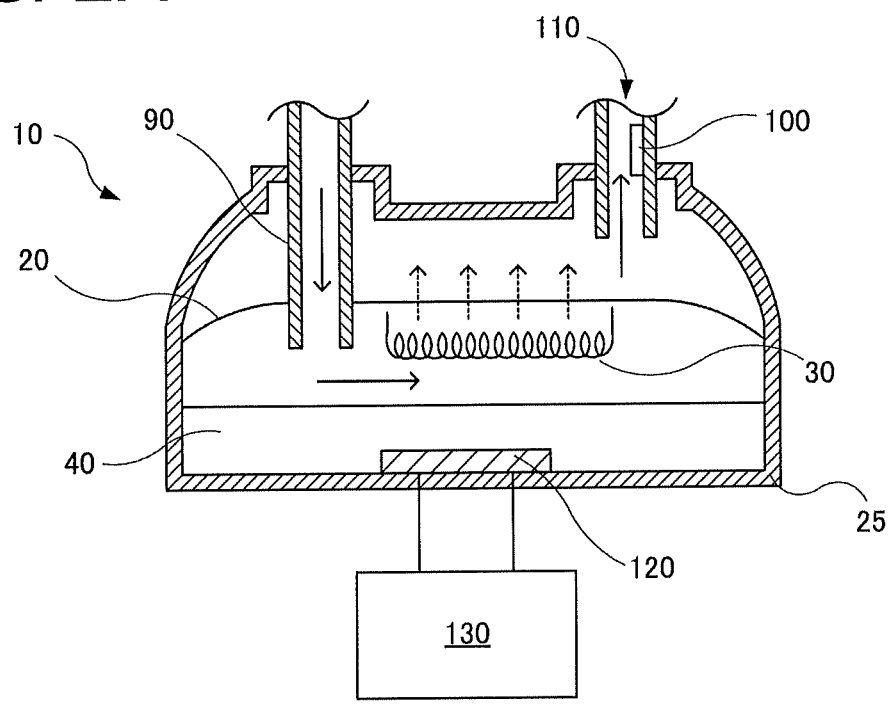
FIG. 2A is a cross-sectional view of a humidifier according to a second embodiment of the present invention.

FIG. 2A is a cross-sectional view of a humidifier 10 according to a second embodiment of the present invention. In the humidifier 10, water 40 is stored in a case 25. A water retaining member 20 partitions a droplet heating unit 30 and the water 40 from a breathing circuit-side pipe 110. The water retaining member 20 is made of a nonwoven fabric. The water retaining member 20 is in a plane shape, and is joined to an inner side surface of the case 25 at its end. The water retaining member 20 entirely covers the liquid 40. A gas fed from a ventilator-side pipe 90 necessarily passes through the water retaining member 20. The ventilator-side pipe 90 is disposed inside the water retaining member 20, in other words, so as to feed the gas to the side of the liquid 40. A mist-droplet generation unit 70 of the humidifier 10 is a steam-type mist-droplet generation unit having a liquid heating unit configured to heat the liquid to vaporize the water 40 contained in the liquid. As in the case of the aforementioned first embodiment, the droplet heating unit 30 configured to heat at least one of mist droplets and moisture held by the water retaining member to vaporize the mist droplets or moisture into water vapor is disposed inside the water retaining member 20, in other words, on the side of the water 40. The droplet heating unit 30 is a resistance heater made of, for example, a nichrome wire or the like, and is controlled by the controller 130 at a predetermined temperature. As with the conventional humidifier 10, the present second embodiment adopts a method in which the water 40 is vaporized by heating to increase vapor pressure. Since humidification can be performed while the water stored in the liquid container is sterilized, the humidifier is easily kept in a good hygiene state, and the fed gas is filtered by the water retaining member 20. In other words, the water retaining member 20 has the effect of playing a role as a bacteria filter, as well as a humidifier.

The droplet heating unit 30 may be integrally formed with the water retaining member 20, or may be provided outside the water retaining member 20, in other words, on the side of an inspiratory pipe or on the side of the case. The positional relationship between the water retaining member 20 and the droplet heating unit 30 is the same as those in the other embodiments and modification embodiments. The droplet heating unit 30 may be disposed inside or outside the water retaining member 20, and the water retaining member 20 and the droplet heating unit 30 may be integrated with each other.

Figure 2B:
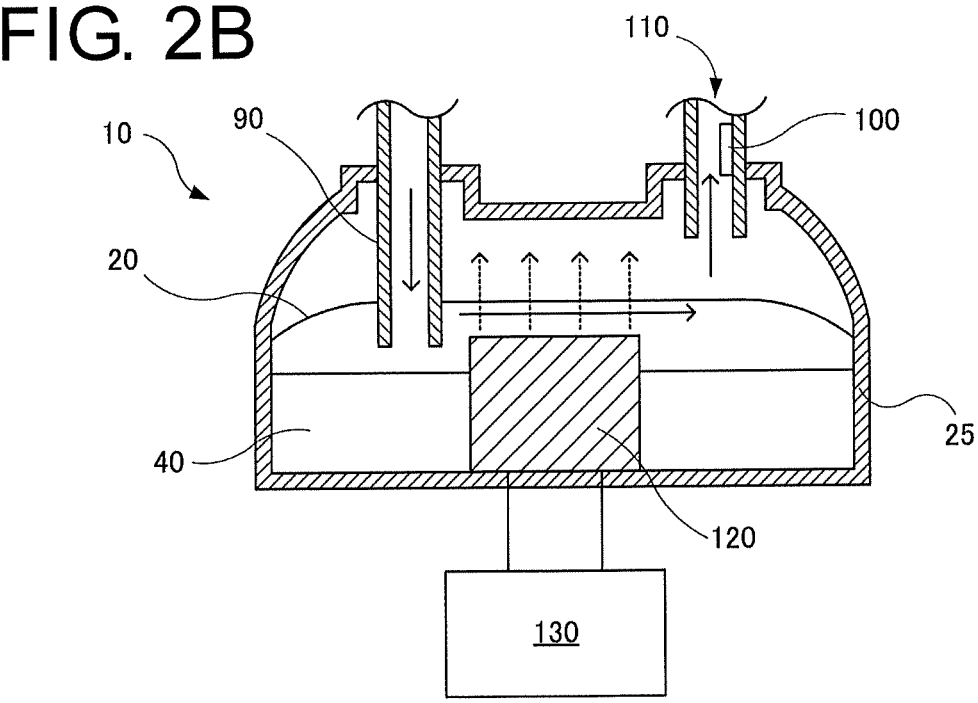
FIG. 2B is a cross-sectional view of a modification example of the humidifier.

FIG. 2B shows a humidifier 10 according to a modification embodiment of the second embodiment of the present invention. In the present modification embodiment, a liquid heating unit constituting the mist-droplet generation unit 70 is a heating unit 120 that is integrated with the droplet heating unit 30 configured to heat at least one of the mist droplets and moisture held by the water retaining member to vaporize the mist droplets or moisture. In other words, a part of the heating unit 120 is exposed upward from a liquid surface, to heat at least one of the mist droplets and the moisture held in the water retaining member to vaporize the mist droplets or moisture. The heating unit 120 is, for example, a resistance heater, and is controlled by a controller 130 at a predetermined temperature. Since the mist-droplet generation unit 70 and the droplet heating unit 30 are integrated, the present embodiment has the beneficial effect of facilitating temperature control. The vapor pressure of the gas fed from the ventilator-side pipe 90 is increased with the water vapor vaporized by the heating unit 120. The gas is filtered by the water retaining member 20, and is fed to the breathing circuit-side pipe 110.

Figure 3:
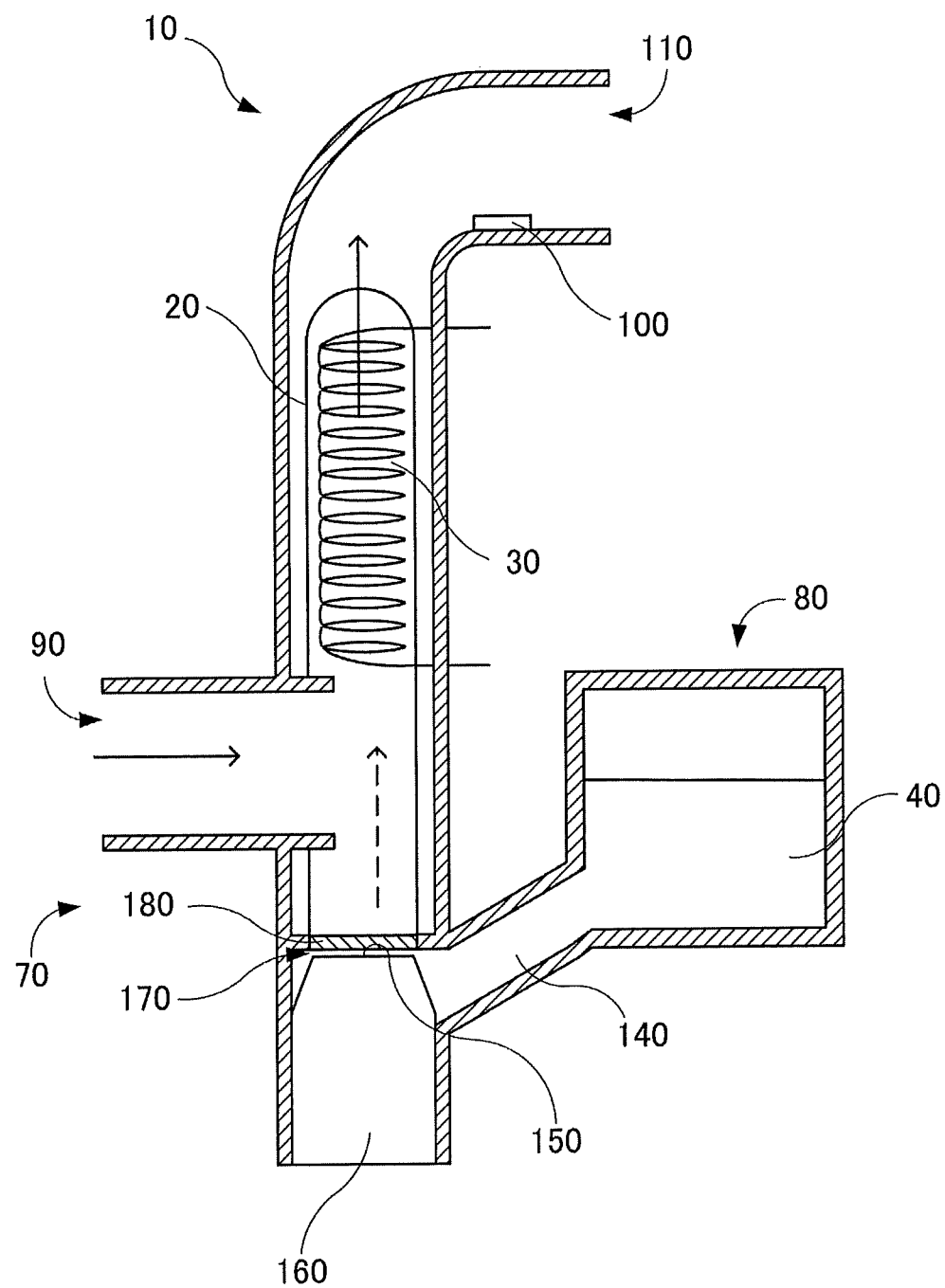
FIG. 3 is a cross-sectional view of a humidifier according to a third embodiment of the present invention.

FIG. 3 is a cross-sectional view showing a configuration of a humidifier 10 according to a third embodiment of the present invention. A mist-droplet generation unit 70 of the humidifier 10 has the same configuration as a mesh-type spraying unit, which is a unit configured to realize a nebulizer (a device configured to generate minute mists containing pharmaceutical drugs for an aerosol inhalation therapy or a nebulization therapy). The mist-droplet generation unit 70 includes a vibration generation device 160 and a mesh 180 having many minute pores. A gap between an oscillator 150 of the vibration generation device 160 and the mesh 180 is filled with water 170. By causing the vibration generation device 160 to vibrate, mist droplets are generated. The advantages of this configuration are small size and good controllability. Therefore, the humidifier 10 can be made extremely compact as a whole, and accordingly, the respiratory assistance device 1 has good transportability. There is also an advantage that the mist droplets can be generated from a small amount of water. The mist droplets generated by the mesh-type mist-droplet generation unit 70 are heated by the droplet heating unit 30, and are vaporized into water vapor to humidify a gas fed from the ventilator-side pipe 90.

Figure 4:
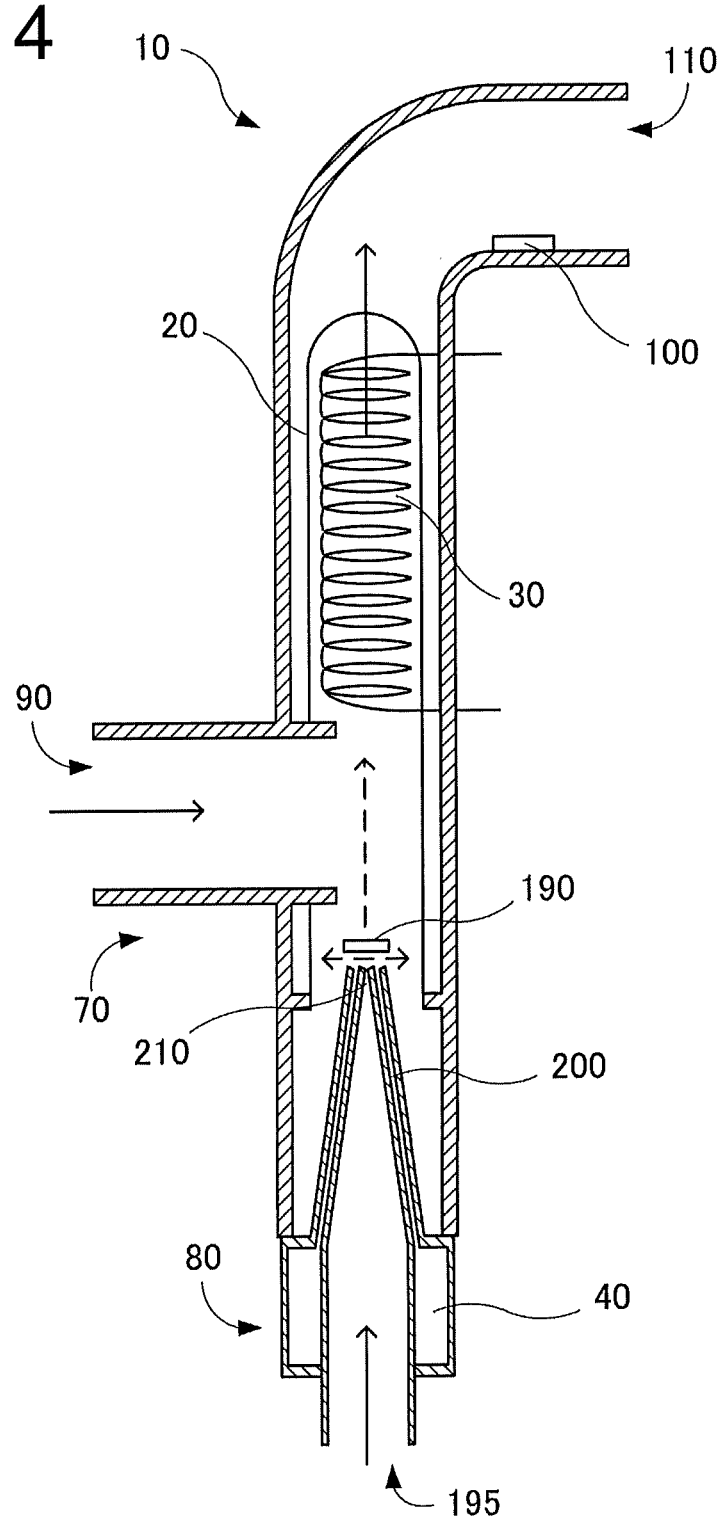
FIG. 4 is a cross-sectional view of a humidifier according to a fourth embodiment of the present invention.

FIG. 4 is a cross-sectional view showing a configuration of a humidifier 10 according to a fourth embodiment of the present invention. A mist-droplet generation unit 70 of the humidifier 10 has the same configuration as a spraying unit of a so-called compressor-type or jet-type nebulizer. When compressed air fed from a compressor-side pipe 195 is ejected at high speed from a nozzle 210, ambient pressure is reduced using the Venturi effect, and water 40 is sucked up from a water inlet pipe 200. The sucked water 40 lively bumps against a baffle 190 to generate mist droplets. The humidifier having the jet-type mist-droplet generation unit 70 using the compressed air offers the advantages of ease in structure, ease in maintenance, ease in keeping in a good hygiene state. The mist droplets generated by the mist-droplet generation unit 70 are heated by the droplet heating unit 30, and are vaporized into water vapor to humidify a gas fed from the ventilator-side pipe 90.

FIG. 5A is a cross-sectional view showing a configuration of a humidifier 10 according to a fifth embodiment of the present invention. In the present embodiment, no droplet heating unit 30 is present. The humidifier 10 includes a case 25, a mist-droplet generation unit 70, a liquid container 80, and a water retaining member 20. FIG. 5A shows an example in which the mist-droplet generation unit 70 has the ultrasonic generation unit configured to generate mist droplets by applying vibration to liquid. However, the mist-droplet generation unit 70 may have a liquid heating unit configured to heat the liquid to vaporize water contained in liquid 40, to generate mist droplets, may have a mesh-type mist-droplet generation unit, or may have a jet-type mist-droplet generation unit.

The humidifier 10 has a passage configured to allow fed gas to pass therethrough. The passage is closed by the water retaining member 20. The water retaining member 20 partitions the passage into an upstream side that is on the side of a gas source (ventilator) 280 and has the liquid container 80 and the mist-droplet generation unit 70, and a downstream side that is on the side of a user. To be more specific, an end part of the water retaining member 20 is joined to the case 25 so as to close the passage. The water retaining member 20 blocks the mist droplets, while allowing a gas containing water vapor to pass therethrough.

FIG. 5B shows a modification embodiment of the water retaining member 20 shown in FIG. 5A. FIG. 5B is a cross-sectional view taken along line A-A of FIG. 5A, i.e. sectioned in a virtual plane represented by alternate short and long dashed lines. In the present modification embodiment, a plurality of holes through which gas containing mist droplets can pass are formed in the water retaining member 20. When a user inspires a gas having a relative humidity of 100% at a low temperature and a low absolute humidity value, the gas absorbs moisture in a respiratory tract, while being humidified in the respiratory tract. This may cause fixation of secretion and the like in a wide area extending to a peripheral respiratory tract. However, since the mist droplets are liquid fine particles that are irrelevant to vapor pressure, the gas containing the mist droplets contains a large amount of moisture, as a result. Therefore, the present modification embodiment has an advantage that there is no possibility of drying up the inside of the respiratory tract. The present modification embodiment offers the above beneficial effect, owing to the plurality of holes through which the gas containing the mist droplets can pass.

FIG. 5C is a cross-sectional view of a humidifier according to a sixth embodiment of the present invention. In the present embodiment, a plurality of water retaining members 20 is provided, and each of the water retaining members 20 partially closes a passage. To be more specific, the water retaining members 20 are configured to have a shape protruding perpendicularly from a case 25 to a passage, for example, in a staggered manner, such that a gas containing mist droplets does not flow without any obstacle. According to this shape, the mist droplets collide against the water retaining members 20, and are held in the water retaining members 20. A gas containing water vapor is fed to a user with less resistance.

Figure 6:
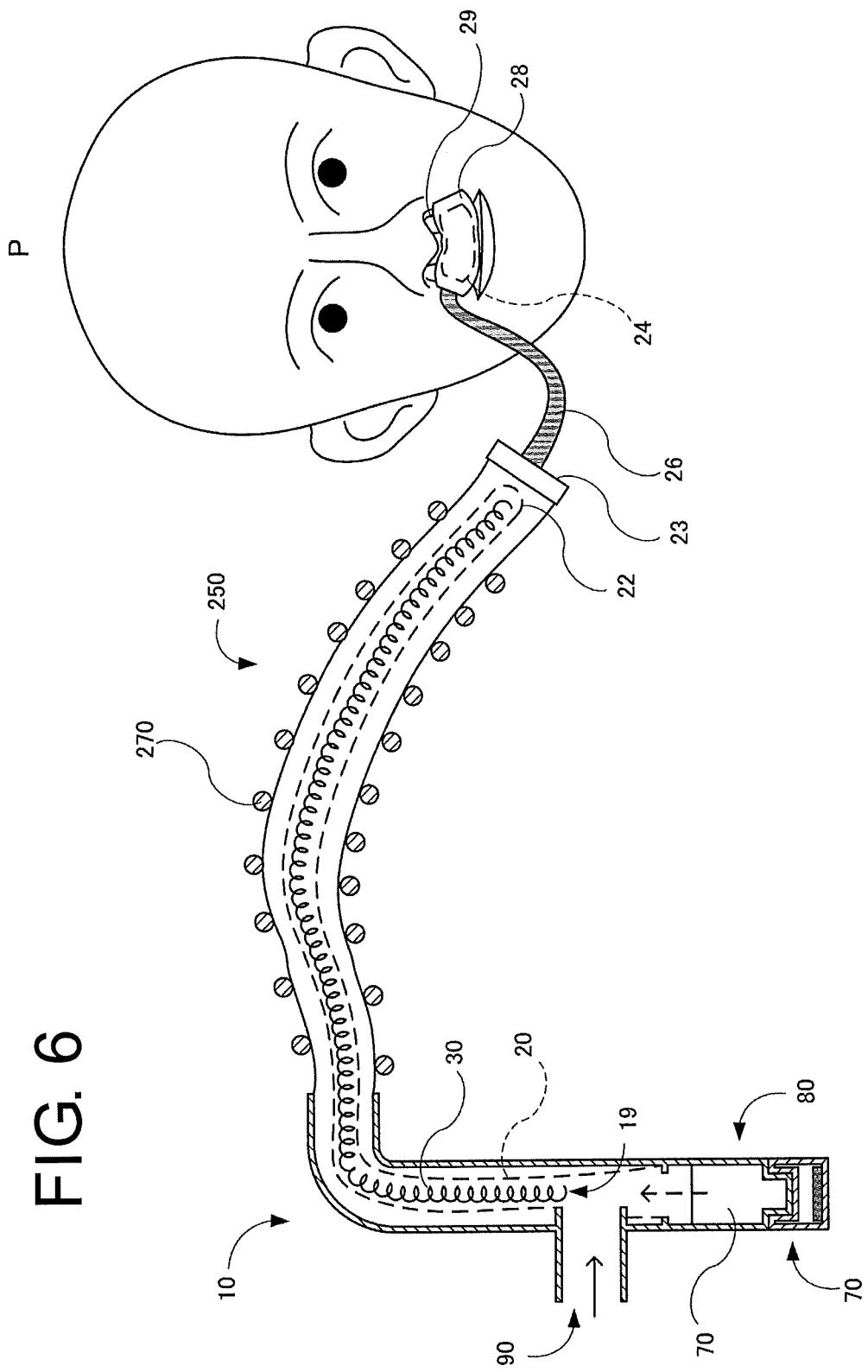
FIG. 6 is an explanatory view of a respiratory assistance device according to a seventh embodiment of the present invention, in which a water retaining member is disposed in an inspiratory pipe of a breathing circuit.

FIG. 6 is an explanatory view of a humidifier 10 according to a seventh embodiment of the present invention. Components of the humidifier 10 are the same as those of the aforementioned first embodiment. The humidifier 10 includes a liquid container 80 that is disposed between the ventilator-side pipe 90 and the breathing circuit-side pipe 110 and contains liquid including at least water, a mist-droplet generation unit 70 configured to generate mist droplets, i.e. minute droplets of the liquid, and a water retaining member 20 configured to hold at least a part of the mist droplets.

The inspiratory pipe 250 is connected to a pipe 26 through a connector 23, and the pipe 26 is connected to a housing 28. A gas is fed into nasal cavities of a user P through a nasal prong 29 supported by the housing 28.

Inside the housing 28, a water retaining member 24 is provided as a droplet absorbing unit. When condensation occurs in the vicinity of the nasal prong 29, droplets may enter a respiratory tract together with the fed medical gas. Since bacteria tend to occur in liquid water, the entry of the droplets into the respiratory tract may cause pneumonia. Disposing the water retaining member 24 in the vicinity of the nasal prong 29 has the significant effect of preventing the droplets from entering the respiratory tract, by absorbing the condensed droplets.

Note that the water retaining member 20 is preferably divided into at least two members, which are disposed separately. The water retaining member 20 on the side of the humidifier 10 is always supplied with mist droplets, and is in a wet state, in principle. On the contrary, the water retaining member 24 disposed in the vicinity of the nasal prong 29 aims at absorbing droplets, and is preferably dry. Therefore, by dividing the water retaining member 20 into at least two members, i.e. into the water retaining member 20 and the water retaining member 24, as shown in FIG. 6, the water retaining members can play different roles as a water retaining member for humidification and a water retaining member for absorption.

A major feature of the present embodiment is that the water retaining member 20 extends to the inside of the inspiratory pipe 250. Specifically, the water retaining member 20 is provided inside the inspiratory pipe of the breathing circuit provided to the respiratory assistance device 1 along a longitudinal direction, and the length of the water retaining member 20 is 50 cm or more. For sufficient humidification, irrespective of a gas flow rate, the length of the water retaining member 20 is preferably 50 cm or more, and more preferably 1 m or more. According to this configuration, the water retaining member 20 has an extremely wide surface area, thus having the extremely significant effect of facilitating vaporization of moisture held in the water retaining member 20. If the water retaining member 20 containing moisture is present along an inner wall of the inspiratory pipe 250, when the inspiratory pipe 250 of the breathing circuit is heated with an anti-condensation heater attached thereto, the majority of the heat is used for evaporating the moisture from the water retaining member 20, thus having the beneficial effect of preventing an increase in temperature of the inspiratory pipe 250.

Figure 8:
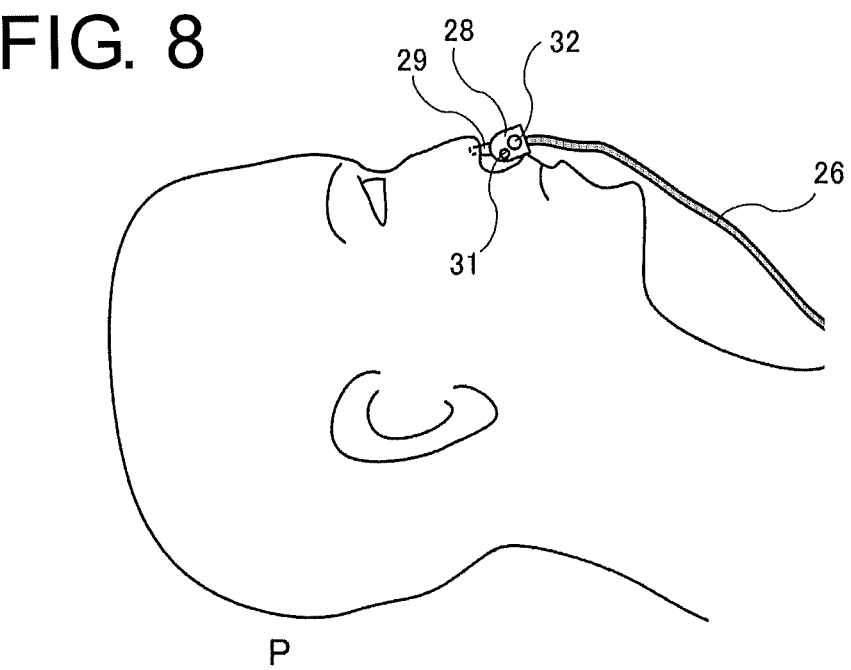
FIG. 8 is a partly enlarged explanatory view of a respiratory assistance device according to an eighth embodiment of the present invention, in which a water retaining member is disposed in a housing that supports a nasal prong configured to feed air to a user and a drain hole is provided therein.

The water retaining member 20 has gas permeability, and has a tubular structure that is closed at one end on the side of the user P, i.e. a water retaining member end part 22, and is open at the other end on the side of the gas source (ventilator) 280. The gas penetrates the inside of the water retaining member 20 through an opening 19, passes through the water retaining member, and is released into the inspiratory pipe 250. In the present embodiment, the droplet heating unit 30, configured to heat the mist droplets and the moisture held in the water retaining member 20 to vaporize them into water vapor, is provided inside the water retaining member 20. The droplet heating unit 30 is controlled by a controller 130 (not illustrated) at a predetermined temperature. The droplet heating unit 30 is a resistance heater made of, for example, a nichrome wire or the like. The droplet heating unit 30 controls temperature and humidity using the controller 130 on the basis of the temperature detected by a thermometer (not illustrated) and the like provided in the inspiratory pipe 250. As shown in FIG. 8, when the water retaining member 20 is made of a soft material, providing the droplet heating unit 30 in an inscribed manner in the water retaining member 20 facilitates keeping the shape of the water retaining member 20. In other words, a space is maintained inside the water retaining member 20, thus having the effect of keeping a sufficient surface area for evaporation.

When the water retaining member 20 has a net-shaped structure such as mesh, the diameters of mesh pores are preferably smaller than the diameters of mist droplets.

As a modification embodiment, the droplet heating unit 30 may be provided in a circumscribed manner on the water retaining member 20, or the droplet heating unit 30 may be embedded in fibers constituting the water retaining member 20. In addition to providing the droplet heating unit 30 in the vicinity of the water retaining member 20, the droplet heating unit 30 may be provided in an inscribed or circumscribed manner in or on the inspiratory pipe 250 itself of the breathing circuit provided in a respiratory assistance device. When the gas is fed at a low flow rate, in particular, an anti-condensation heating unit 270 of the inspiratory pipe 250 that doubles as a droplet heating unit 30, without providing the droplet heating unit 30 in the vicinity of the water retaining member 20, produces a sufficient humidification effect.

Figure 7A:
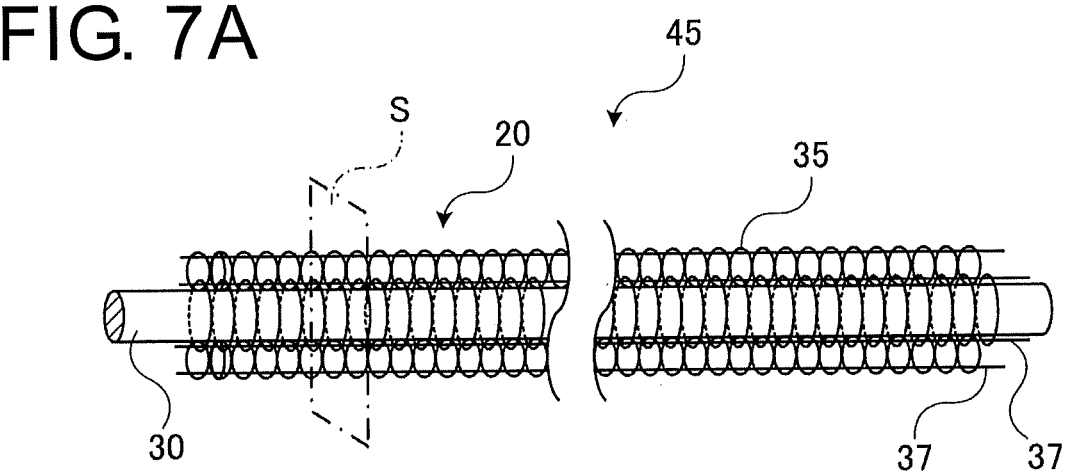
FIG. 7A is an explanatory view of a humidification member that humidifies the respiratory assistance device according to the seventh embodiment of the present invention.

FIG. 7A is an explanatory view of a humidification member 45 that extends to the inside of the inspiratory pipe 250 in the respiratory assistance device according to the seventh embodiment. The droplet heating unit 30 in FIG. 6 is a coil heater, but the droplet heating unit 30 in FIG. 7A is a linear resistance heater. The humidification member 45 includes the droplet heating unit 30 and a water retaining member 20. The water retaining member 20 is made of woven fibers 35. The shape of the water retaining member 20 is stabilized by a core 37. The core 37 may be made of the same material as the fibers 35, or may be made of thicker fibers than the fibers 35 constituting the water retaining member 20. The fibers preferably have an affinity for water, but may be hydrophobic. Droplets are caught inside the fibers 35 or between the fibers 35. The fibers are preferably soft and easily deformable by fingers even in a woven state. The caught moisture is heated by the droplet heating unit 30 to become water vapor, and is supplied to the user P through the medical gas.

Figure 7B:
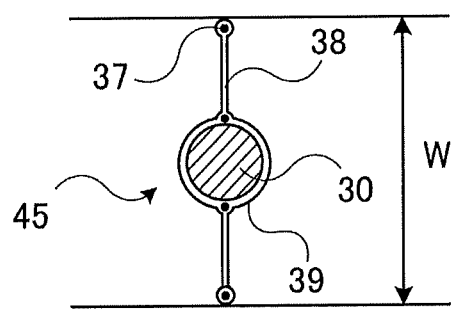
FIG. 7B is a cross cross-sectional view of the humidification member.

FIG. 7B is a cross-sectional view of the humidification member 45 taken along a virtual plane S perpendicular to the droplet heating unit 30 (see FIG. 7A). The water retaining member 20 made of woven fibers 35 is provided with plate-shaped parts 38 and a pipe-shaped part 39 configured to cover the droplet heating unit 30. The width W of the humidification member 45 is preferably 5 mm or more. The provision of the plate-shaped parts 38 has the effect of increasing the area of members that easily contain droplets. As a matter of course, the water retaining member 20 may be made only of the pipe-shaped part 39 configured to cover the droplet heating unit 30, in effect.

Figure 7C:
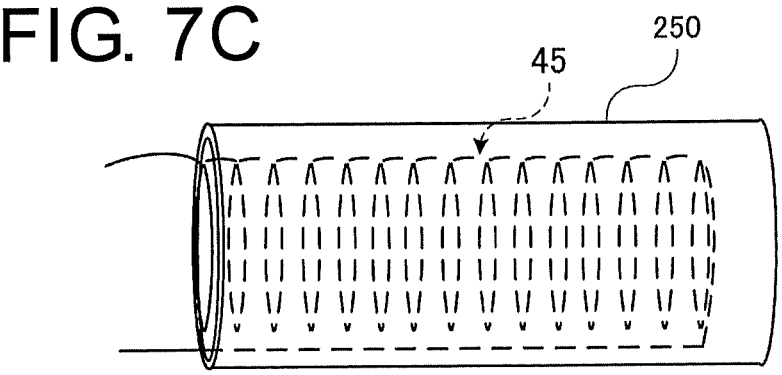
FIG. 7C is an explanatory view of a structure in which a humidification member formed into a coil shape is disposed in a pipe of the breathing circuit.

FIG. 7C is an explanatory view of a structure in which a humidification member formed into a coil shape is disposed in a hose 250 of the breathing circuit. FIG. 7C shows only a part of the hose 250. The humidification member 45 is disposed inside the hose 250 in a state of being wound into a coil shape. The humidification member 45 is preferably inscribed in the hose 250. According to this configuration, the water retaining member 20 can absorb water droplets adhering to an internal wall of the hose 250, and the water droplets can be made into water vapor by being heated by the droplet heating unit 30.

When the water retaining member 20 has the shape of FIG. 7A, a shield member, such as the water retaining member 20 shown in FIG. 5A, that allows gas to pass therethrough while catching droplets, is preferably disposed inside or in the vicinity of the humidifier 10 in such a manner as to block a flow path so that droplets contained in the fed medical gas do not directly reach the lungs of the user P. The water retaining member 20 may be made of a nonwoven fabric. In this case, the water retaining member 20 preferably covers the droplet heating unit 30 in a tubular manner.

FIG. 8 is a partly enlarged explanatory view of a respiratory assistance device according to an eighth embodiment of the present invention. A nasal prong 29 is inserted into nasal cavities of a user P, and a medical gas is fed from a pipe 26 to the user P through a housing 28 configured to support the nasal prong 29. The housing 28 configured to support the nasal prong 29 has a drain hole 31. The drain hole 31 is preferably provided in the housing 28 at a position near the user P, such that, when the user P lies down, accumulated droplets easily drain.

Although a water retaining member 24 (not illustrated) is disposed inside the housing 28, droplets beyond absorption drain out of the housing 28 through the drain hole 31. When pipe attachment holes 32 are provided on both sides of the housing 28 to connect a pipe 26 therethrough and the pipe attachment hole 32 is clogged with a plug, it is conceivable to provide a drain hole 31 in the plug itself. The pipe attachment hole 32 may double as the drain hole 31.

Embodiments of the present invention are not limited to the embodiments described above, but can be variously modified, as a matter of course, without departing from the scope of the present invention. As a modification example of each of the embodiments, it is conceivable to apply the following embodiment.

Figure 9:
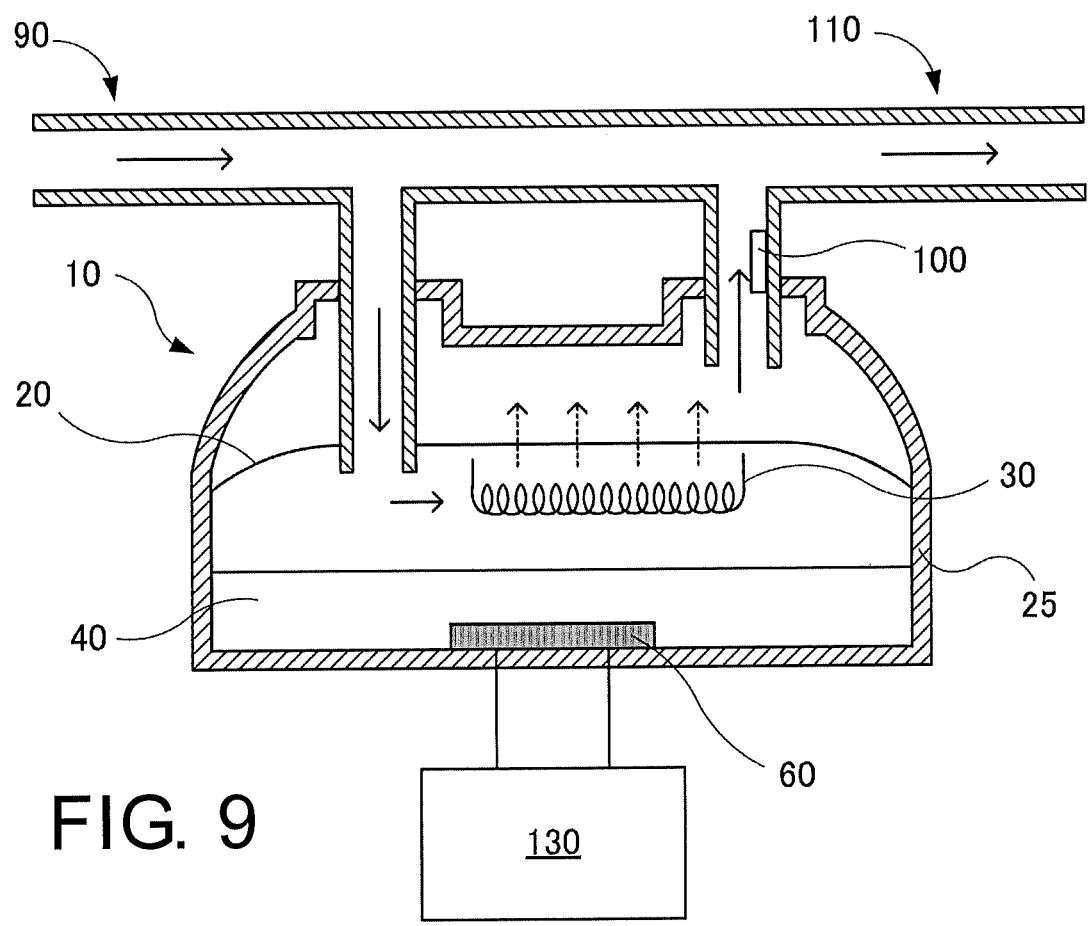
FIG. 9 is an explanatory view of a respiratory assistance device having a branch to a humidifier, according to a modification embodiment of the present invention.

In the above-described embodiments, the entire gas humidified with the water vapor generated in the liquid container 80 is fed into the breathing circuit-side pipe 110, after being filtered with the water retaining member 20. However, a part of the fed gas may pass through the inside of the water retaining member 20, while the remaining part of the gas may not pass through the inside of the water retaining member 20. For example, as shown in FIG. 9 as a modification example of the present invention, a part of a gas fed from the ventilator-side pipe 90 may be branched upstream of the humidifier 10, and may be merged with humidified gas downstream of the humidifier 10 at a breathing circuit on the side of a user. The modification embodiment has the effect of reducing a resistance load of breathing.

REFERENCE SIGNS LIST 1 respiratory assistance device
10 humidifier
20 water retaining member
22 water retaining member end part
23 connector
24 water retaining member
25 case
26 pipe
28 housing
29 nasal prong
30 droplet heating unit
31 drain hole
32 pipe attachment hole
35 fiber
37 core wire
38 plate-shaped part
39 pipe-shaped part
40 water
45 humidification member
50 ultrasonic transfer material
55 case
60 ultrasonic oscillator
70 mist-droplet generation unit
80 liquid container
85 boundary
90 ventilator-side pipe
100 thermometer
110 breathing circuit-side pipe
120 heating unit
130 controller
140 water feeding pipe
150 oscillator
160 vibration generation device
170 water
180 mesh 190 baffle
195 compressor-side pipe
200 water inlet pipe
210 nozzle
220 humidification chamber
230 expiratory pipe
240 thermometer
250 inspiratory pipe (hose)
260 mask
270 anti-condensation heating unit
280 gas source (ventilator)
290 heater
S virtual plane

The invention claimed is:

1. A humidifier that is to be connected to a respiratory assistance device configured to regulate or assist ventilation of a user, the humidifier being configured to add moisture to a gas fed from a gas source in the form of fine particles or water vapor, the humidifier comprising:
    a liquid container configured to contain a liquid containing at least water;
    a mist-droplet generation unit configured to generate mist droplets being fine particles of the liquid; and
    a water retaining member configured to hold at least a part of the mist droplets;
    wherein a part of the gas passes through an inside of the water retaining member, and a remaining part of the gas does not pass through the inside of the water retaining member.

2. The humidifier according to claim 1, wherein one end of the water retaining member that is open on the side of the gas source is joined to an inner peripheral surface of the humidifier, and the water retaining member closes a passage through which the gas flows.

3. The humidifier according to claim 2, wherein the humidifier has the passage through which the gas flows, the passage is closed by the water retaining member, and the water retaining member partitions the passage into an upstream side that is on a side of the gas source and has the liquid container and the mist-droplet generation unit, and a downstream side that is on a side of the user.

* * * * *